(12) United States Patent
Alex et al.

(10) Patent No.: US 6,352,717 B2
(45) Date of Patent: Mar. 5, 2002

(54) PROCESS FOR ENCAPSULATING SHEAR SENSITIVE FILL MASSES INTO CAPSULES AND CAPSULES CONTAINING SHEAR SENSITIVE FILL MASSES

(75) Inventors: Rainer Alex, Weil am Rhein (DE); Jürgen Gerhards, Arlesheim (CH); Ingeborg Kraemer-Pittrof, Rheinfelden (DE); Richard Oeschger, Rheinsulz (CH); Thomas Rades, Dunedin (NZ)

(73) Assignee: Hoffman-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/440,731

(22) Filed: Nov. 16, 1999

(30) Foreign Application Priority Data

Nov. 17, 1998 (EP) .............................. 98121831

(51) Int. Cl.⁷ ............................ A61K 9/48; A61K 9/66; A61K 9/64
(52) U.S. Cl. ........................ 424/451; 424/455; 424/456
(58) Field of Search ................................ 424/451, 456, 424/455

(56) References Cited

U.S. PATENT DOCUMENTS 2,692,404 A * 10/1954 Plourde et al.
5,723,452 A * 3/1998 Chan ........................ 514/155
5,876,749 A * 3/1999 Al-Razzak et al. ......... 424/456

FOREIGN PATENT DOCUMENTS

| DE | 85 36 337 U | 2/1986 |
| EP | 0 040 840 A | 12/1981 |
| EP | 0 227 060 B1 | 7/1987 |

OTHER PUBLICATIONS

J. P. Stanley, The Theory and Practice of Industrial Pharmacy, pp. 398–412 (1986).

L. L. Augsburger, Hard and Soft Shell Capsules, pp. 395–428 (1996).

* cited by examiner

*Primary Examiner*—Thurman K. Page
*Assistant Examiner*—S. Tran
(74) *Attorney, Agent, or Firm*—George W. Johnston; Patricia S. Rocha-Tramaloni; Eileen M. Ebel (57) ABSTRACT

The present invention provides a process for encapsulating a shear sensitive fill mass which contains a pharmaceutical active agent or nutrient, characterized in that said fill mass is heated and subsequently cooled, prior to the encapsulation. The invention also provides capsules comprising shear sensitive fill material obtained by the said process which have a high and constant dissolution rate.

16 Claims, 6 Drawing Sheets

PROCESS FOR ENCAPSULATING SHEAR SENSITIVE FILL MASSES INTO CAPSULES AND CAPSULES CONTAINING SHEAR SENSITIVE FILL MASSES

BACKGROUND OF THE INVENTION

Owing to their special properties and advantages, gelatin capsules are used widely in the pharmaceutical industry. They can be applied as an oral dosage form, as a suppository dosage form for rectal use or for vaginal use, as a specialty package in tube form, for human and veterinary single dose application, in the cosmetic industry etc. Their capsule shell is basically composed of gelatin and water; it may contain additional ingredients such as plasticisers, preservatives, colouring and opacifying agents, flavouring, sugars, acids, and medicaments to achieve desired effects.

Gelatin capsules can be used to dispense a variety of different active compounds. Several advantages of gelatin capsules derive from the fact that the drug may be a liquid or at least dissolved, solubilised, or suspended in a liquid vehicle. Since the capsule fill mass is metered into individual capsules by a positive-displacement pump, a much higher degree of reproducibility is achieved than is possible with powder or granule feed in the manufacture of tablets and powder or granule filled hard gelatin capsule products. The biopharmaceutical availability of drugs formulated as liquid filled gelatin capsules, as measured by disintegration time or dissolution rate, often shows an advantage over other solid dosage forms. The biopharmaceutical characteristics of such formulations can be altered or adjusted more easily than those of other dosage forms. Through the selection and use of liquids and combinations of liquids that range from water immiscible through emulsifiable to completely water-miscible, and by altering the type or quantity of thickening or suspending agents, capsule formulations allow more flexibility in the design of a dosage form to fit biopharmaceutical specifications of a particular therapeutic agent.

Mainly, two different kinds of gelatin capsules are commonly used, i.e. soft and hard gelatin capsules.

Several processes are known in the art for producing soft gelatin capsules. The most important is the rotary die process, which is a continuous flow process developed by Scherer first in 1933 (J. P. Stanley, *The Theory and Practice of Industrial Pharmacy*, $3^{rd}$ Ed., 1986, p 398–412).

According to this process, the gelatin mass is fed by gravity to a metering device (spreader box), which controls the flow of the mass onto air-cooled rotating drums. Gelatin ribbons of controlled thickness are therefore formed. The ribbons are fed through a lubricating bath, over guide rolls, and then down between an injection wedge (for the fill material) and die rolls. The material to be encapsulated, which has been previously mixed and stored, flows by gravity into a positive displacement pump. The pump accurately meters the material through a leads and the wedge and into the gelatin ribbons between the die rolls. The capsule is about half sealed when the pressure of the pumped material forces the gelatin into the die pockets, where the capsules are simultaneously filled, shaped, hermetically sealed and cut from the gelatin ribbon. The sealing of the capsule is achieved by mechanical pressure on the die rolls and the heating of the ribbons by the wedge. All fill masses (e.g. liquids, solutions, and suspensions) for encapsulation should preferably flow at room temperature and in any case at a temperature not exceeding 35° C. at the point of encapsulation, since the sealing temperature of the gelatin films must remain below this temperature.

Several types of filling machines for hard gelatin capsules are known in the pharmaceutical industry (Larry L. Augsburger, Hard and Soft Shell Capsules, Modern Pharmaceutics, G. S. Banker, C. T. Rhodes (Eds.), Third Edition, Marcel Dekker Inc. (1996), 395–428).

The liquid fill mass can be prepared as described for the soft gelatin capsules process. The empty capsules, comprising a cap and a body portion, are oriented so that all point in the same direction (i.e. body-end downward). In general the capsules pass one-at-a-time through a channel just wide enough to provide a frictional grip at the cap end. A specially designed blade pushes against the capsule and causes it to rotate about its cap end as a fulcrum. After two pushes (one horizontally and one vertically downward), the capsules will always be aligned body-end downward, regardless of which end entered the channel first. At this point the caps are separated from the bodies. Here, the rectified capsules are delivered body-end first into the upper portion of split bushings or split filling rings. A vacuum applied from below pulls the bodies down into the lower portion of the split bushing. The diameter of the caps is too large to allow them to follow the bodies into the lower bushing portion. The split bushings are then separated to expose the bodies for filling. The body portion of the capsule can be thus filled with the fill mass which cannot exceed a temperature of 60° C. The cap and body bushing portions are rejoined wherein pins are used to push the filled bodies up into the caps for closure, and to push the closed capsules out of the bushings. Compressed air also may be used to eject the capsules. If necessary, hard gelatin capsules may be made hermetically by e.g. banding (i.e. layering down a film of gelatin, often distinctively colored, around the seam of the cap and body).

Using the above mentioned processes, however, it has been unfortunately found that shear sensitive fill masses can totally or partially solidify before being encapsulated, or even in the capsules upon storage. The solidification of the fill mass or of one or more components thereof is due to mechanical phenomena, such as the shear stress, which occurs at various points of the manufacturing process. The most critical points of the process involve the mixing vessels and the pumps, wherein the shear stress dramatically increases with increasing viscosity of the fill mass.

This total or partial solidification can cause significant and unacceptable changes in the pharmaceutical quality of the product like, for example, reduction and variability of the capsules dissolution rate, and hence the bioavailability of the drug substance and the therapeutic effects of the drug.

SUMMARY OF THE INVENTION

The present invention provides a process for encapsulating a shear sensitive fill mass into a capsule, comprising the following steps in order:

a) providing a shear sensitive fill mass comprising an agent taken from the group consisting of pharmaceutical active agents and nutrients;

b) heating the fill mass;

c) cooling the fill mass; and d) encapsulating the fill mass into the capsule essentially immediately after said cooling.

The present invention provides a capsule containing a shear sensitive fill mass which comprises an agent selected from the group fo pharmaceutically active agents and nutrients, wherein the fill mass is encapsulated in accordance with the above process.

The present invention also provides a capsule containing a shear sensitive fill mass which comprises an agent selected from the group of pharmaceutically active agents and nutrients, wherein the capsule has a constant dissolution rate of at least 70% of the pharmaceutically active agent within 30 minutes after administration.

DETAILED DESCRIPTION OF THE INVENTION

The present invention provides a process for encapsulating shear sensitive fill masses into capsules and capsules containing shear sensitive fill masses obtained by said process. The fill mass comprises a pharmaceutically active agent or a nutrient.

The term "capsule" encompasses hard and soft shell capsules which are preferably used to administer nutrients or pharmaceutically active agents to individuals. Such capsules are soluble under physiological conditions, digestible or permeable. The capsule shells are usually made of gelatin, starch, or other suitable physiologically acceptable macromolecular materials in form of gels. Examples thereof are soft gelatin capsules, hard gelatin capsules and Hydroxy Propyl Methyl Cellulose (HPMC) capsules.

A shear sensitive fill mass which undergoes the process of the present invention can be an emulsion, dispersion or solution including a supersaturated solution. Suitable vehicles which can be used for preparing fill masses for encapsulation may be chosen among the aromatic and aliphatic hydrocarbons, chlorinated hydrocarbons, high-molecular-weight-alcohols, esters and organic acids, vegetable oils, mineral oil, silicon oil, non-ionic surface active agents, polyethylene glycols, medium chain triglycerides and medium chain mono and diglycerides, either alone or in combination.

The solid component of the shear sensitive fill mass, which has formed due to shear stress during the mixing and pumping stages of the process, can be re-liquefied or re-dissolved by heating it. The temperature to which the fill mass must be heated depends on the physical and chemical characteristics of the fill mass itself. The fill mass is then cooled to below about the sealing temperature for the type of capsule being used, so that the temperature of the fill mass is below the sealing temperature of the capsule when the fill mass is placed in the capsule.

Since the encapsulation temperature for soft and hard gelatin capsules should usually not exceed 35° C. and 60° C., respectively, the homogeneous fill mass is cooled to below the stated temperature for each type of gelatin capsule, preferably to about room temperature. It has been surprisingly found that, once cooled, the homogeneous shear sensitive fill mass does not return to the solid or semi-solid state as long as it does not undergo further mechanical strain. According to the present invention, the encapsulation takes place within a sufficiently short amount of time after the heating and subsequent cooling of the shear sensitive fill mass so that the content of the capsule remains homogeneous over the life time of the encapsulated nutrient or pharmaceutical agent. The heating and subsequent cooling of the fill mass takes place essentially immediately prior to encapsulation. For example, the amount of time from the cooling step to the encapsulation step can be from about 10 to 30 seconds, preferably from about 10 to about 20 seconds. The heating and cooling of the fill mass can be carried out in conventional manners, e.g. by letting it flow through spiral tubes immersed in water/oil baths and cold water bath, respectively. As the contact time of the fill mass in the heating device can be varied by modifying the residence time in the bath, heating of the fill mass after it has been processed through the dosing pump is also suitable for thermolabile substances.

The process according to the present invention allows one to obtain capsules showing high and constant dissolution rates. The amount of active agent encapsulated and administered to a patient can be therefore reduced since the active agent itself is rapidly dissolved. The overall costs of the medicaments are thereby also reduced. The high homogeneity (and therefore the high and constant dissolution rate) of the capsules produced with the process according to the present invention guarantees a reproducible bioavailability and therapeutic effect of an active agent which is contained in it.

In the case in which the capsule is made of soft gelatin, the fill mass is preferably heated to a temperature between 0° C. and about 20° C. above its melting point, and subsequently cooled to a temperature between about 35° C. and about 20° C. Where hard gelatin capsules are produced, the fill mass is preferably heated to a temperature between 0° C. and about 20° C. above its melting point, and subsequently cooled to a temperature between about 60° C. and about 20° C.

The process according to the present invention is suitable for fill masses like, for instance, emulsions, dispersions and solutions comprising the pharmaceutically active agent(s), as well as for pure pharmaceutically active agents in the liquid state. Particularly, the process according to the present invention is suitable for fill masses comprising high doses of a sparingly soluble pharmaceutical agent such as e.g. a HIV protease inhibitor and, more particularly, for solutions of saquinavir. These particular fill masses can be heated to a temperature which is preferably in the range between about 70° C. and about 100° C. and then cooled to a temperature between about 35° C. and about 20° C., in the case of soft gelatin capsules, and between about 60° C. and about 20° C. in the case of hard gelatin capsules.

Preferably, the process according to the present invention comprises the steps of:
a) feeding the fill mass into a feed tank;
b) feeding the fill mass from the feed tank into a dosing pump;
c) dosing the fill mass through a heater and then a cooler and into an injection wedge;

d) injecting the heated and subsequently cooled fill mass of step c) from the injection wedge into the capsules.

To advantage, the fill mass undergoes heating also in the feed tank, at a temperature which is preferably between about 35° C. and about 95° C. In this way solidification of the fill mass in the dosing pump can be avoided, and any complete or partial solidification of the fill mass that has occurred prior to the dosing pump can be reversed. In addition, heating of the feed tank reduces the viscosity of the fill mass and therefore reduces the risk and extent of solidification of the fill mass caused by shear stress in the dosing pump.

In accordance with a preferred embodiment of the present invention, the fill mass undergoes heating in the dosing pump, at a temperature which is preferably between about 35° C. and about 80° C. The heating of the dosing pump, e.g. electrically, avoids solidification of the fill mass in the dosing pump or reverses solidification of the fill mass that has occurred prior to the dosing pump. As the contact time of the fill mass in the dosing pump is short, heating of the latter is also suitable for thermolabile substances.

In a particularly preferred embodiment of the present invention, the fill mass is heated in the feed tank, as well as in the dosing pump, preferably at the above temperatures.

In accordance with the preferred process of the present invention, the fill mass which flows from the dosing pump is heated and then cooled. The dosed amounts are then passed into an injection wedge for subsequent injection into the capsules.

By using the process of the present invention, capsules are obtained wherein the shear sensitive fill mass remains highly homogeneous for at least six to twelve, or even up to about 24 months after production. The capsules obtained according to the process of the invention contain a shear sensitive fill mass and have a constant dissolution rate, and release of at least 70% of the drug substance is achieved within 30 minutes after administration.

The capsules according to the present invention contain a shear sensitive fill mass and which have a constant dissolution rate of at least 70% of the drug substance within 30 minutes after administration.

The fill mass preferably contains, as active ingredient, a HIV protease inhibitor and, more preferably, a solution of saquinavir.

By way of example, a preferred embodiment of the present invention is described with reference to the accompanying figures.

Figure 1A:
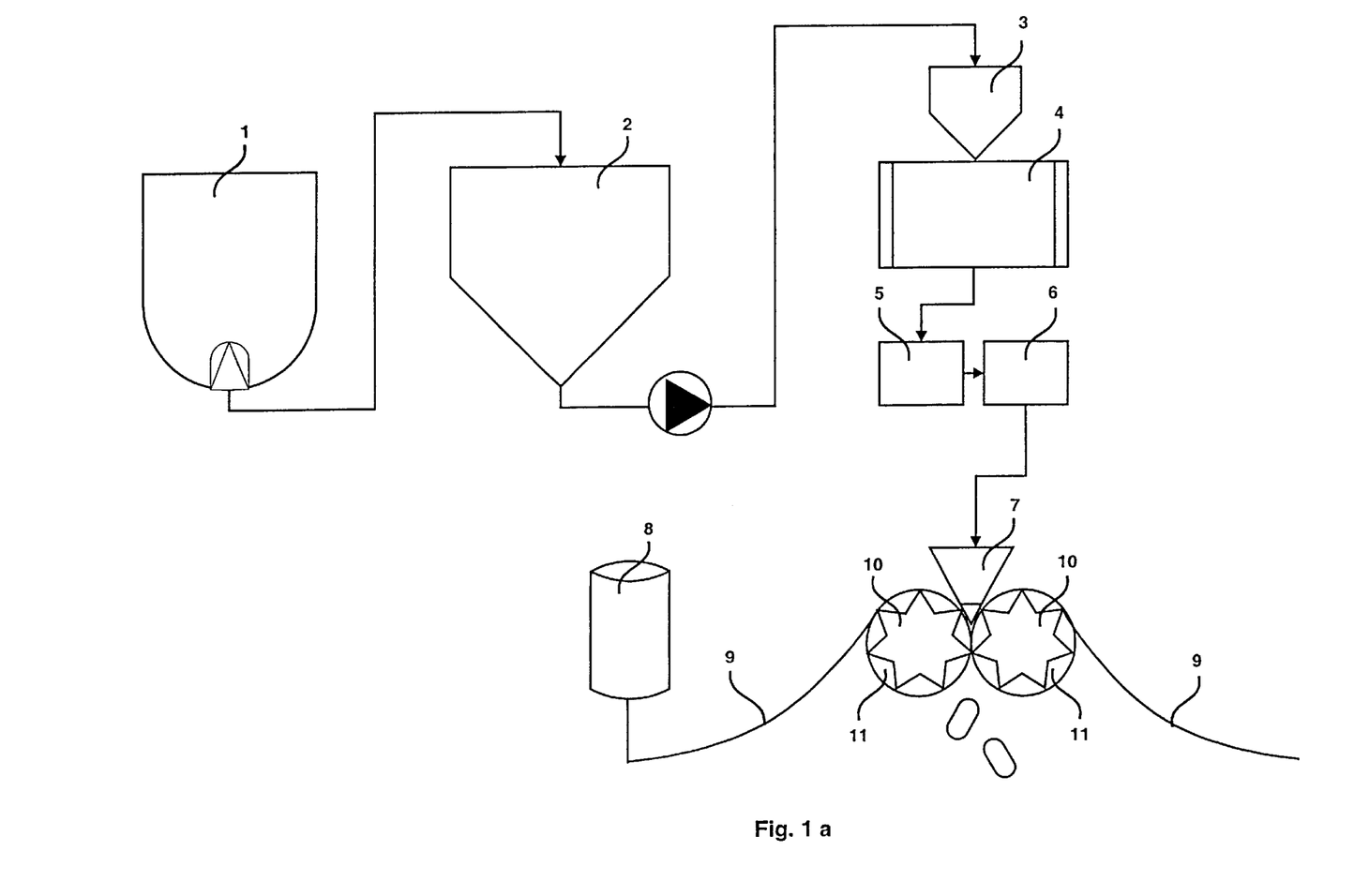
FIG. 1a is a flow sheet diagram depicting the process according to the invention for manufacturing soft gelatin capsules.
Figure 1B:
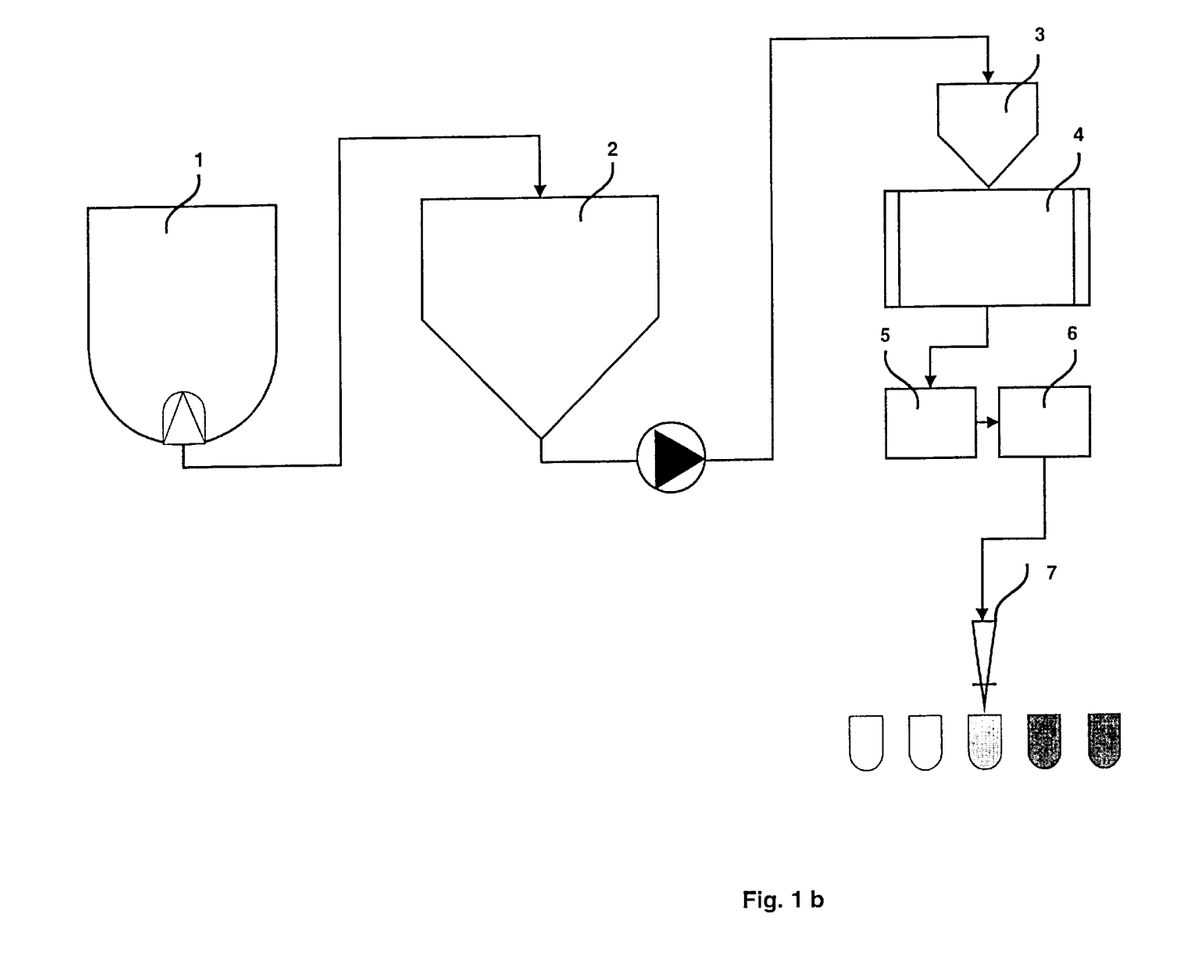
FIG. 1b is a flow sheet diagram depicting the process according to the invention for manufacturing hard gelatin capsules.

Referring now to FIGS. 1a and 1b, the fill mass is prepared in a mixing vessel 1, wherein the active agent is dissolved, emulsified or suspended in an appropriate solvent, eventually together with antioxidants and/or other additives. The so obtained solution, emulsion or suspension, is transferred into a storage tank 2, and then pumped into a feed tank 3 and heated by a water bath. From the feed tank 3, the fill mass is fed by gravity to an electrically heated dosing pump 4 controlling the flow of the mass which will be injected in the capsules. The fill mass flowing out from the dosing pump 4 undergoes heating in a heating bath 5 (oil or water) and afterwards cooling in a cooling bath 6 (cold water) and is finally fed to a filling wedge 7 for injection into the capsule.

For the manufacture of soft gelatin capsules (FIG. 1a), gelatin mass is fed by gravity to a metering device 8 which controls the flow of the mass onto rotating drums (not shown). Gelatin ribbons 9 of controlled thickness are thus formed. The ribbons 9 are fed through a lubricant bath (not shown), over guide rolls (not shown) and then down between the wedge 7 and die rolls 10.

The fill mass is dosed, through orifices (not shown) of the wedge 7 into the gelatin ribbons 9 between the die rolls 10, wherein the orifices are lined up with die pockets 11 of the die rolls 10. The capsule is about half sealed when the pressure of the pumped fill mass forces the gelatin into the die pockets 11, where the capsules are simultaneously filled, shaped, hermetically sealed and cut from the gelatin ribbons 9. The sealing of the capsule is achieved, by mechanical pressure on the die rolls 10 and by heating of the gelatin ribbons 9 by the wedge 7.

For the manufacture of hard gelatin capsules (FIG. 1b), the fill mass is dosed through orifices (not shown) of the wedge 7 into previously prepared hard gelatin shells 8. The filled hard gelatin capsules are then sealed.

EXAMPLE

Saquinavir gelatin capsules having the composition listed in Table 1 were prepared according to the process already described.

TABLE 1a

Composition of saquinavir soft gelatin capsule

| Ingredient | mg/Capsule |
|---|---|
| Capsule Fill: | |
| Saquinavir (amorphous) | 200.00 |
| Medium Chain Mono and Diglycerides | 765.00 |
| Povidone K 30 | 30.00 |
| DL-alpha-Tocopherol | 5.00 |
| Mass of capsule contents | 1000.00 |
| Capsule Shell: | |
| Gelatin | 250.92 |
| Glycerol 85% | 168.73 |
| Titanium Dioxide | 3.06 |
| Yellow Iron Oxide | 0.20 |
| Red Iron Oxide | 0.027 |
| Mass of capsule shell | 422.937 |

TABLE 1b

Composition of saquinavir hard gelatin capsule

| Ingredient | mg/Capsule |
|---|---|
| Capsule Fill: | |
| Saquinavir (amorphous) | 120.00 |
| Medium Chain Mono and Diglycerides | 459.00 |
| Povidone K 30 | 18.00 |
| DL-alpha-Tocopherol | 3.00 |
| Mass of capsule contents | 600.00 |
| Capsule Shell: | |
| Gelatin | 96.00 |

TABLE 2

Temperature profile in the different plant units

| Plant unit | Temperature profile |
|---|---|
| Mixing vessel 1 (under stirring) | 75–105 min at 63° C. |
| | 5 min at 83° C. |
| | cooling at 28° C. |
| Storage tank 2 | 25° C. |
| Feed tank 3 (in water bath) | 50° C. (bath) |
| | 35–40° C. (fill mass) |

TABLE 2-continued

Temperature profile in the different plant units

| Plant unit | Temperature profile |
| --- | --- |
| Dosing pump 4 | 50° C. (pump) |
| | 40° C. (fill mass) |
| Heating bath 5 | 90° C. (bath) |
| | to 90° C. within 2 min (fill mass) |
| Cooling bath 6 | 20° C. (bath) |
| | to 30–25° C. (fill mass) |
| Filling wedge 7 | 25° C. (fill mass) |

The optical density and the light scattering of the capsule content (C) obtained with the process according to the invention were measured. Table 3 shows the values of the content (C) of three soft gelatin capsules obtained with the process of the invention and of the content of three soft gelatin capsules obtained with a conventional process (i.e., without heating the fill mass in the feed tank or in or after the dosing pump).

TABLE 3

Optical Density (540 nm, 5 × 5 mm cell) and Light Scattering (500/500 nm, 5 × 5 mm cell).

| | Conventional Process | | | Process according to the invention | | |
| --- | --- | --- | --- | --- | --- | --- |
| | C1 | C2 | C3 | C1 | C2 | C3 |
| Optical Density | 0.862 | 1.391 | 0.343 | 0.010 | 0.014 | 0.008 |
| Light Scattering | 34.3 | 23.8 | 23.8 | 0.010 | 0.010 | 0.000 |

As shown in Table 3, the optical density and the light scattering values of the capsule content produced according to the above process are much lower than those obtained with conventional processes and, they are highly reproducible. The saquinavir capsules of Table 3 obtained with the process of the present invention are therefore superior in their homogeneity and limpidity as compared to those obtained with conventional processes.

Figure 2:
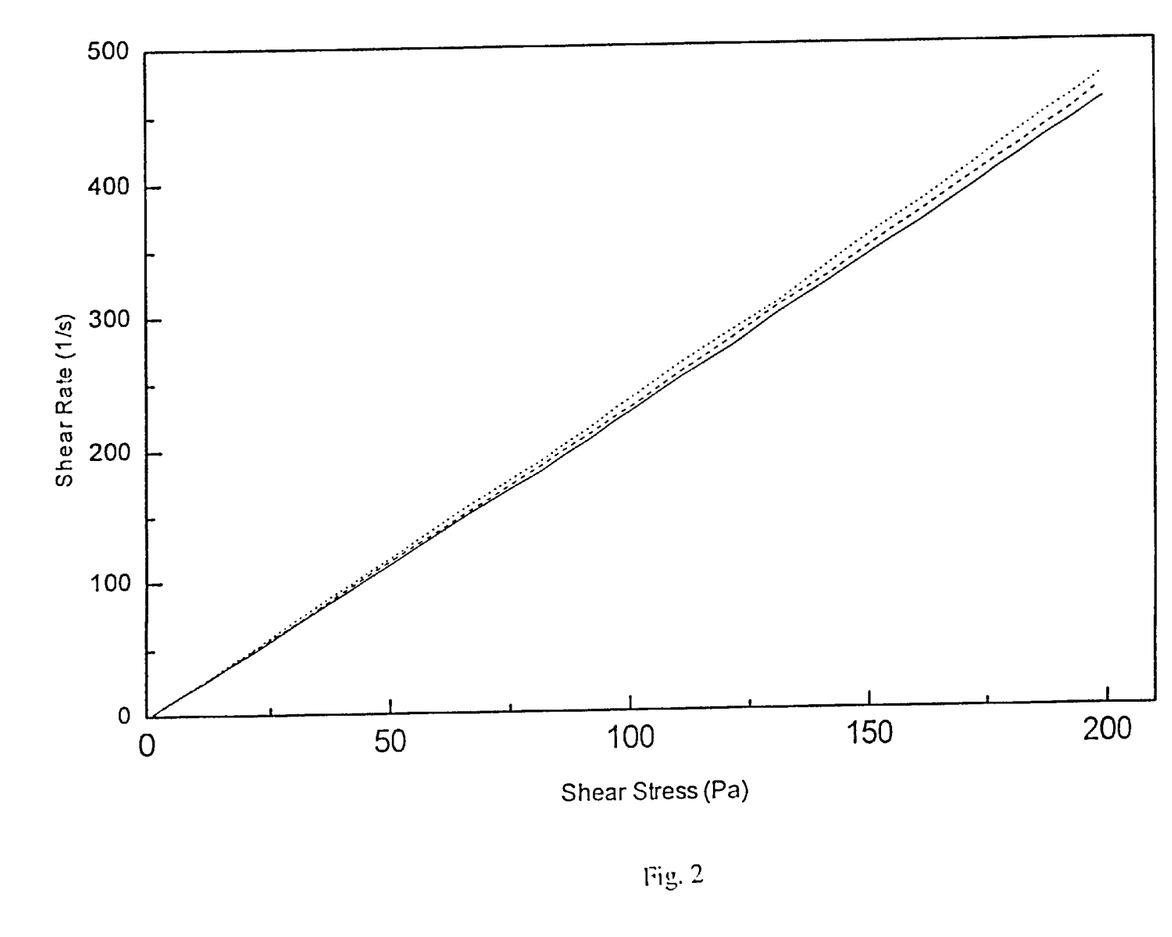
FIG. 2 is a rheogramm of the shear stress (Pa) over the shear rate (1/s) of three saquinavir soft gelatin capsules manufactured with the process of the invention.
Figure 3:
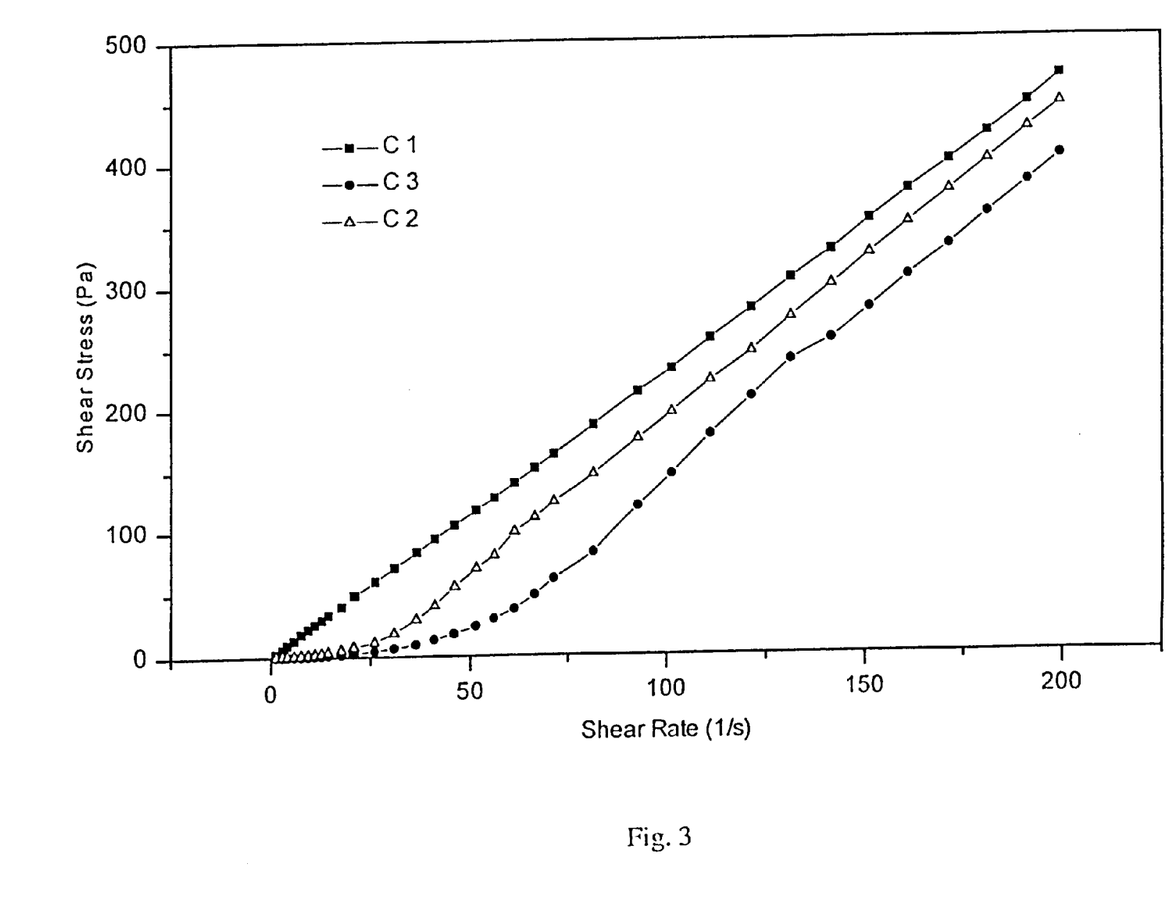
FIG. 3 is a rheogramm of the shear stress (Pa) over the shear rate (1/s) of a saquinavir soft gelatin capsule (C1) manufactured with the process of the invention, and of two saquinavir soft gelatin capsules (C2, C3) obtained with the conventional process.

In FIGS. 2 and 3 (C1) it can moreover be seen that the fill masses of the capsules obtained with the above process are Newtonian liquids, i.e., there is a linear relationship between shear rate and shear stress wherein the flow curves are linear from the origin, whereas the fill masses of capsules manufactured with conventional processes do not show such a behaviour (FIG. 3, C2, C3).

Figure 4:
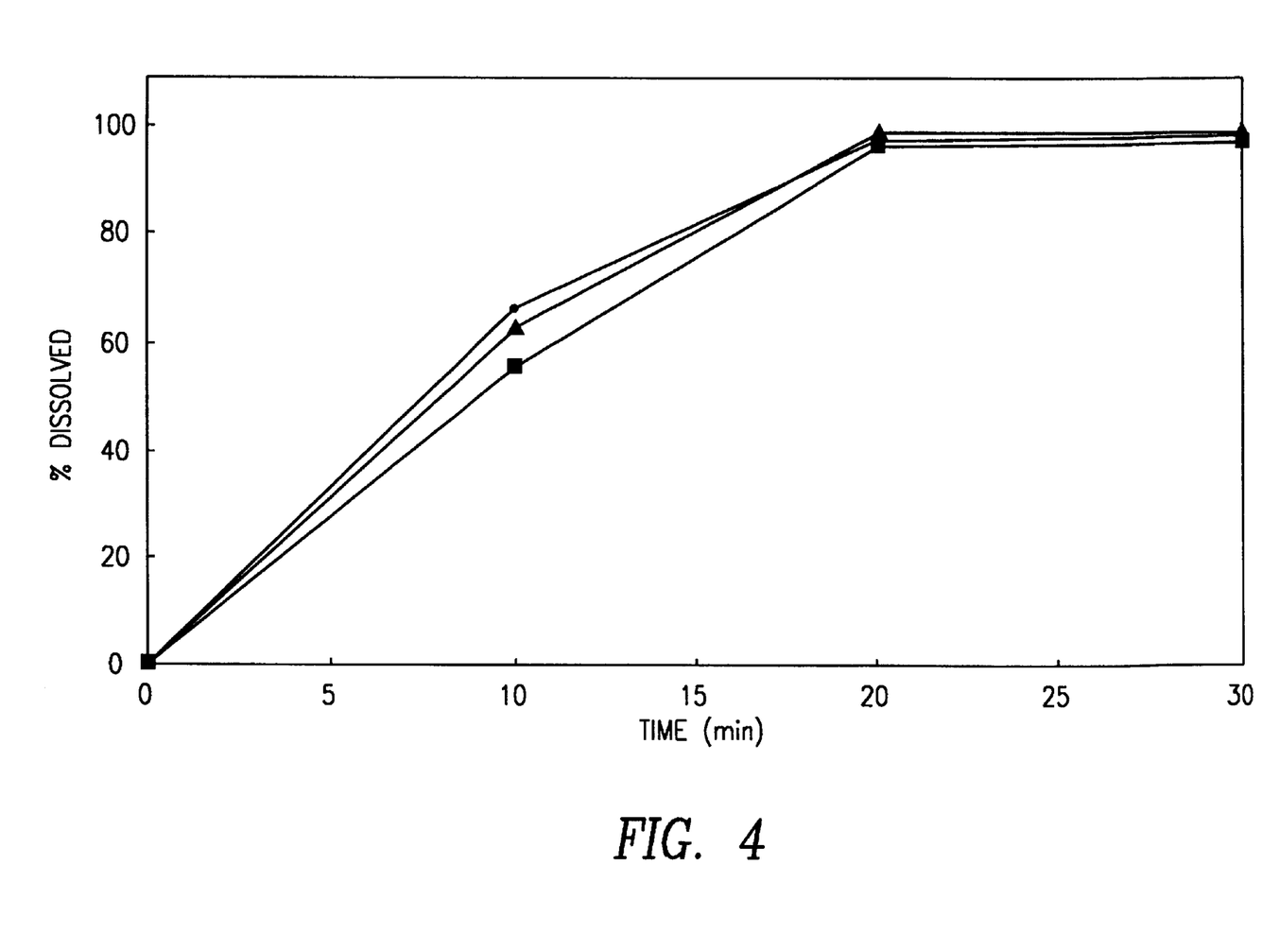
FIG. 4 is the dissolution profile of three saquinavir soft gelatin capsules manufactured with the process of the invention.
Figure 5:
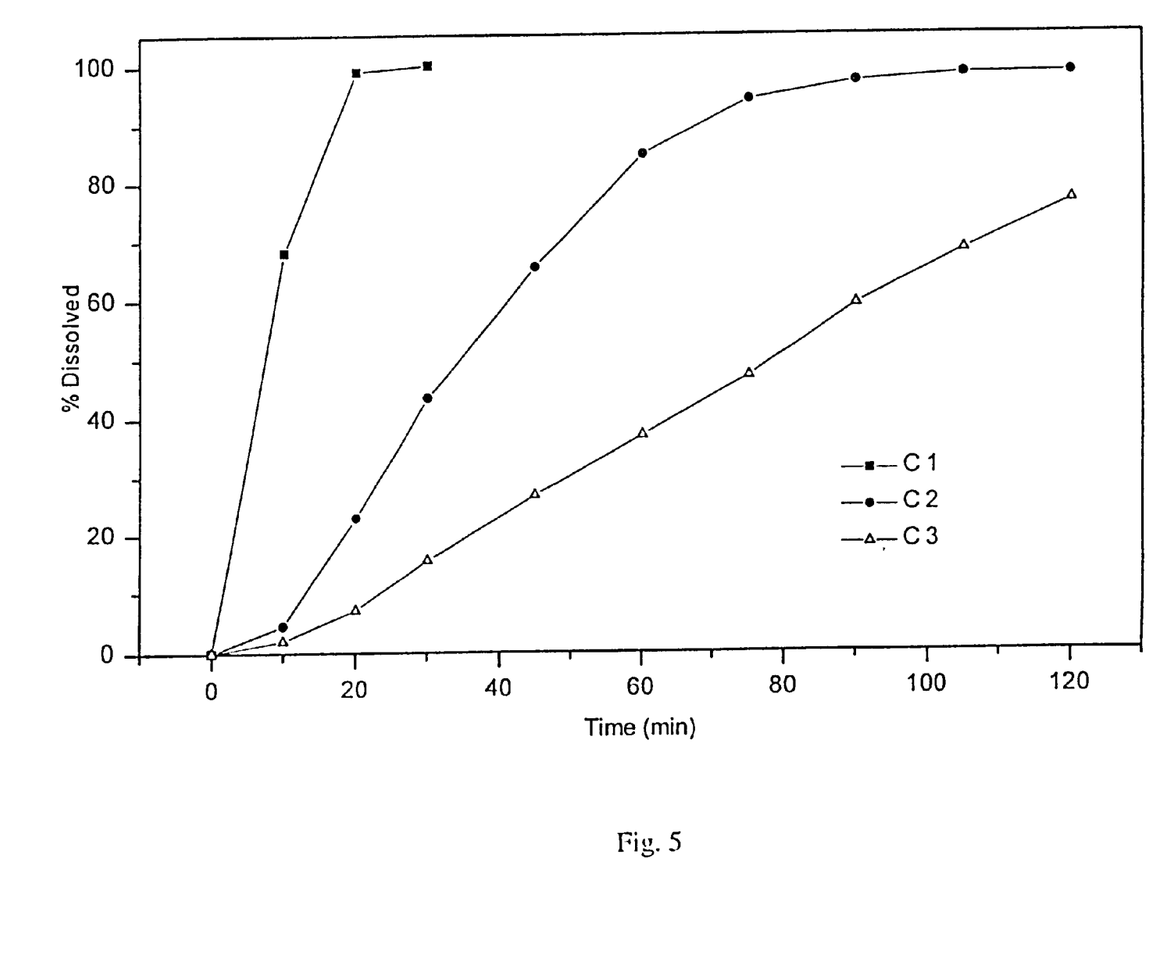
FIG. 5 is the dissolution profile of a saquinavir soft gelatin capsule (C1) manufactured with the process of the invention, and of two saquinavir soft gelatin capsules (C2, C3) obtained with the conventional process.

The saquinavir capsules obtained with the process of the present invention strongly improve their dissolution rate, as compared with conventional capsules. FIG. 5 depicts the much faster dissolution rate of C1, a capsule according to the invention, as compared to the dissolution rate of C2 and C3 which are two capsules made with the conventional technique. FIG. 4 depicts the dissolution profile of three saquinavir soft gelatin capsules manufactured in accordance with the process of the present invention. The dissolution rate of the present saquinavir gelatin capsules is highly reproducible, as clearly shown in FIG. 4.

What is claimed is:

1. A process for encapsulating a shear sensitive fill mass comprising saquinavir into a capsule, comprising the following steps in order:
   a) heating a shear sensitive fill mass selected from the group consisting of emulsions, dispersions and solutions and comprising saquinavir;
   b) cooling the fill mass; and
   c) encapsulating the fill mass into the capsule essentially immediately after said cooling.

2. The process according to claim 1, wherein the capsule is from the group consisting of soft gelatin capsule, a hard gelating capsule and a HPMC capsule.

3. The process according to claim 2, wherein the capsule is a soft gelatin capsule and the fill mass is heated to a temperature between 0° C. and about 20° C. above its melting point, and cooled to a temperature between about 35° C. and about 20° C.

4. The process according to claim 2, wherein the capsule is a hard gelatin capsule and the fill mass is heated to a temperature between 0° C. and about 20° C. above its melting point, and subsequently cooled to a temperature between about 60° C. and about 20° C.

5. The process according to claim 1, wherein said fill mass is heated to a temperature between about 70° C. and about 100° C.

6. The process according to claim 1, wherein the fill mass provided in step a) is a solution.

7. The process according to claim 1, further comprising prior to step a), transporting the fill mass through a pump, to control the flow rate of the fill mass.

8. The process according to claim 7, wherein the fill mass in said pump is heated.

9. The process according to claim 8, wherein the fill mass in said pump is heated to between about 35° C. and about 80° C.

10. The process according to claim 1, further comprising prior to step, a) placing the pharmaceutical fill mass in a chamber and feeding the fill mass from the chamber to a heating unit.

11. The process according to claim 10, wherein the fill mass in said chamber is heated.

12. The process according to claim 11, wherein the fill mass in said chamber is heated to a temperature between about 35° C. and about 95° C.

13. A process for encapsulating a shear sensitive fill mass comprising saquinavir into a capsule comprising the following steps in order:
   a) mixing a shear sensitive fill mass selected from the group consisting of emulsions, dispersions and solutions and comprising saquinavir;
   b) heating the fill mass in a chamber;
   c) transporting the fill mass from the chamber to a pump;
   d) heating the fill mass in the pump;
   e) controlling the flow of the fill mass from the pump;
   f) heating the fill mass from the pump;
   g) cooling the fill mass; and
   h) encapsulating the fill mass into the capsule essentially immediately after said cooling.

14. A capsule containing a shear sensitive fill mass which comprises saquinavir, wherein said fill mass is encapsulated in accordance with the process of claim 1.

15. A capsule containing a shear sensitive fill mass which comprises saquinavir, said capsule having a constant dissolution rate of saquinavir of a least 70% within 30 minutes after administration.

16. A capsule containing a shear sensitive fill mass which comprises saquinavir, wherein the fill mass has a linear relationship between shear rate and shear stress from the origin of a plot of such relationship.

* * * * *

UNITED STATES PATENT AND TRADEMARK OFFICE
CERTIFICATE OF CORRECTION

PATENT NO. : 6,352,717
DATED : March 5, 2002
INVENTOR(S) : Rainer Alex, Jürgen Gerhards, Ingeborg Kraemer-Pittrof, Richard Oeschger and Thomas Rades It is certified that error appears in the above-identified patent and that said Letters Patent is hereby corrected as shown below:

Column 8,
Line 4, "is from the group" should read -- is selected from the group --.

Signed and Sealed this

Twenty-first Day of May, 2002

*Attest:*

JAMES E. ROGAN
*Attesting Officer*     *Director of the United States Patent and Trademark Office*